US007897570B2

(12) United States Patent
Bartlett et al.

(10) Patent No.: US 7,897,570 B2
(45) Date of Patent: Mar. 1, 2011

(54) METHOD OF TREATMENT

(75) Inventors: Perry F. Bartlett, Victoria (AU); Lynne Hartley, Victoria (AU); Mark Pouzzotto, Victoria (AU); Trevor Kilpatrick, Victoria (AU); Frank Kontgen, Western Australia (AU); Jason Coonan, Victoria (AU); Ursula Greferath, Victoria (AU); Andrew W. Boyd, Queenland (AU); Mirella Dottori, Queensland (AU); Mary P. Galea, Victoria (AU); George Paxinos, Victoria (AU); Mark Murphy, Victoria (AU)

(73) Assignees: The Walter and Eliza Hall Institute of Medical Research, Parkville (AU); The Council of the Queensland Institute of Medical Research, Herston (AU); The University of Melbourne, Parkville (AU)

( * ) Notice: Subject to any disclaimer, the term of this patent is extended or adjusted under 35 U.S.C. 154(b) by 5 days.

(21) Appl. No.: 12/007,656

(22) Filed: Jan. 14, 2008

(65) Prior Publication Data
US 2008/0255044 A1 Oct. 16, 2008

Related U.S. Application Data

(63) Continuation of application No. 11/100,716, filed on Apr. 7, 2005, now Pat. No. 7,341,997, which is a continuation of application No. 09/830,319, filed as application No. PCT/AU99/00931 on Oct. 27, 1999, now abandoned.

(30) Foreign Application Priority Data
Oct. 27, 1998 (AU) .......................... PP6748

(51) Int. Cl.
A61K 38/00 (2006.01)
(52) U.S. Cl. .......................... 514/12; 435/377
(58) Field of Classification Search .................. None
See application file for complete search history.

(56) References Cited

U.S. PATENT DOCUMENTS

| 7,341,997 B2 | 3/2008 | Bartlett et al. | |
| 2008/0254023 A1 | 10/2008 | Bartlett et al. | |
| 2008/0255044 A1* | 10/2008 | Bartlett et al. | 514/12 |

FOREIGN PATENT DOCUMENTS

| WO | WO-96/09384 | 3/1996 |
| WO | WO-6/135518 | 5/1996 |
| WO | WO-96/23000 | 8/1996 |
| WO | WO-96/26958 | 9/1996 |
| WO | WO-97/04091 | 2/1997 |
| WO | WO-97/14966 | 4/1997 |

OTHER PUBLICATIONS

Martone et al., Brain research, (Oct. 17, 1997) vol. 771, No. 2, pp. 238-250.*
Flanagan & Vanderhaeghen, Annual Review of Neuroscience, 21:309-345 (1998).*
Park, et al., "Aberrant axonal projections in mice lacking EphA8 (Eek) tyrosine protein kinase receptors", EMBO Journal, 16(11):3106-3114 (1997).
Smith, et al., "The EphA4 and EphB1 receptor tyrosine kinases and ephrin-B2 ligand regulate targeted migration of branchial neural crest cells", Current Biology, 7(8):561-570 (1997).
Richard WS Tsika, Ph.D., "Transgenic Animal Models", Exercises and Sport Science Reviews, 22:361-388 (1994).
Holland, et al., "Cell-contact-dependent signaling in axon, growth and guidance: Eph receptor tyrosine kinases and receptor protein tyrosine phosphatase", Current Opinion in Neurology, 8(1):117-127 (1998).
Brambilla, R. et al., "Telling axons where to grow: a role for Eph receptor tyrosine kinases in guidance", Mol. Cell Neurosci., 6:487-495 (1995).
Tessier-Lavigne, M., Eph receptor tyrosine kinases, axon repulsion, and the development of topographic maps, Cell, 82:345-348 (1995).
Friedman, G. C. et al., "Eph receptor tyrosine kinases and their ligands in neural development", Curr. Opin Neurobiol., 6:127-133 (1996).
Cheng, H. J. et al., "Complementary gradients in expression and binding of ELF-1 and Mek4 in development of the topographic retinotectal projection map", Cell, 82:371-381 (1995).
Drescher, U. et al., "In vitro guidance of retinal ganglion cell axons by RAGS, and 25kDa tectal protein related to ligands for Eph receptor tyrosine kinases", Cell. 82:359-370 (1995).
Nakamoto, M. et al."Topographically specific effects of ELF-1 on retinal axon guidance in vitro and retinal axon mapping in vivo", Cell, 86:755-766 (1996).
Henkemeyer, M. et al., "Nulk controls pathfinding of commissural axons in mammalian central nervous system", Cell, 86:35-46 (1996).
Orioli, D. et al., Sek4 and nuk receptors cooperate in guidance of commissural axons and in palate formation EMBO J, 15:6035-6049 (1996).
Orioli, D. et al., "The Eph receptor family: axonal guidance by contact repulsion", T I G, 13:354-359 (1997).

(Continued)

Primary Examiner — Gary B. Nickol
Assistant Examiner — Daniel C Gamett
(74) Attorney, Agent, or Firm — Foley & Lardner LLP

(57) ABSTRACT

The present invention relates generally to a method of treatment and in particular a method of treating disorders of the nervous system such as arising from or during disease or injury. The method of the present invention involves manipulating expression of Eph receptors or their functional equivalents to increase or decrease expression or function depending on the condition being treated.

4 Claims, 8 Drawing Sheets

OTHER PUBLICATIONS

Figure 1:
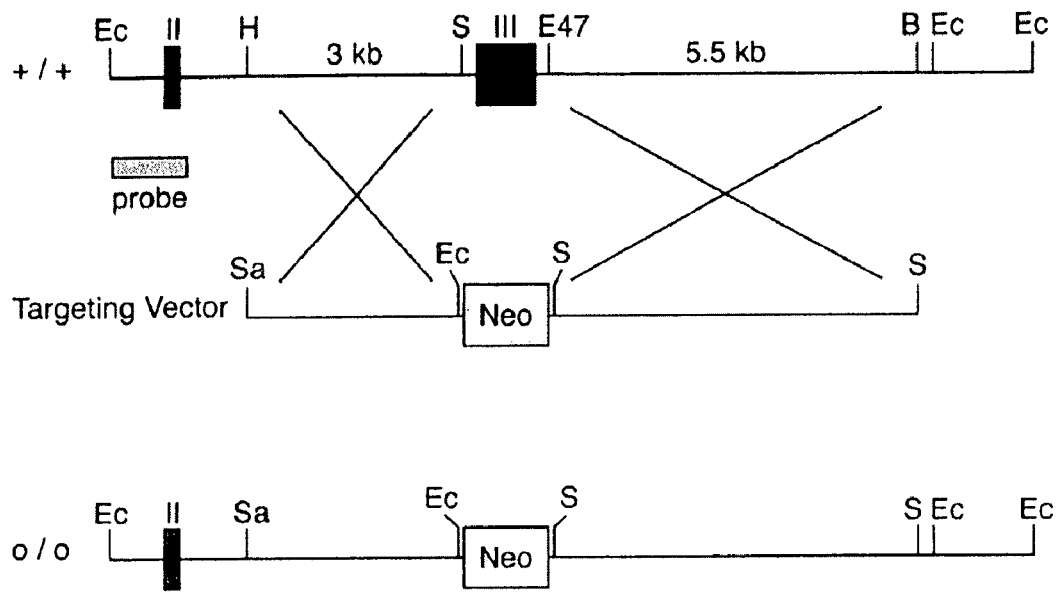
Figure 1:
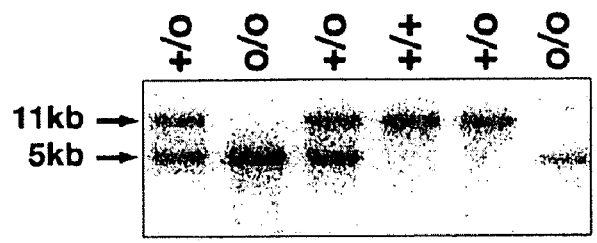
Figure 1:
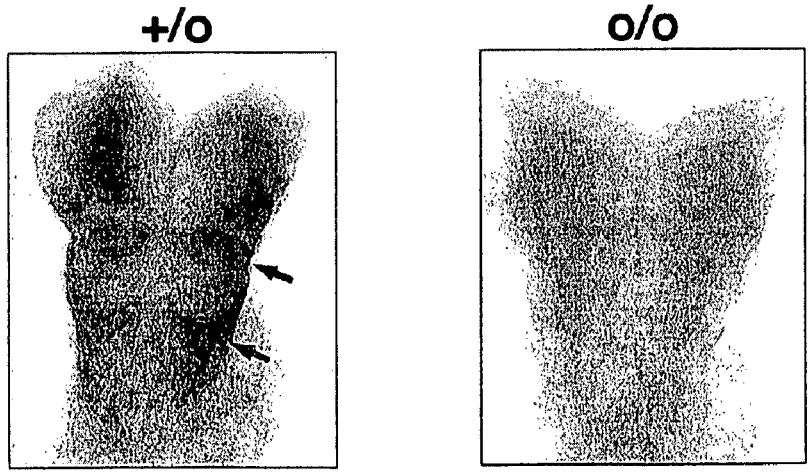

Gale, N. W. et al., "Eph receptors and ligands comprise two major specifically subclasses and are reciprocally compartmentalized during embryogenesis", Neuron, 17:9-19 (1996).

Gale, N. W. et al. "Elk-:L3, a novel transmembrane ligand for the Eph family of receptor tyrosine kinases, expressed in embryonic floor plate, roof plate and hindbrain segments", Oncogene, 13:1343-1352 (1996).

Bergemann, A. D. et al., "Ephrin-B3, a ligand for the receptor EphB3, expressed at the midline of the developing neural tube",. Oncogene, 16:471-480 (1998).

Nieto, M. A. et al, "A receptor protein tyrosine kinase implicated in the segmental patterning of the hindbrain and mesoderm", Development, 116:1137-1150 (1992).

Mori, et al., "Differential expression of the eph family of receptor tyrosine kinase genes (sek, elk, eck) in the developing nervous system of the mouse", Brain Res. Mol. Brain Res.. 29:325-335 (1995).

Xu, Q. et al., "Expression of truncated Sek-1 receptor tyrosine disrupts the segmental restriction of gene expression in the Xenopus and zebrafish hindbrain", Development, 121:4005-4016 (1995).

Xu, Q et al., "Function of the Eph-related kinase rtk1 in patterning of the zebrafish forebrain", Nature, 381:319-322 (1996).

Stanfield, B. B., "The development of the corticospinal projection", Prog. Neurobiol., 38:169-202 (1992).

Irving, C. et al., "Progressive spatial restriction of SEk-1 and Krox-20 gene expression during hindbrain segmentation", Dev. Biol., 173:26-38 (1996).

Robb, L. et al., "Absence of yolk sac hematopoiesis from mice with a targeted disruption of the scl gene", Proc Natl Acad Sci USA, 92 7075-7079 (1995).

Lyons, I. et al. "Myogenic and morphogenetic defects in the heart tubes of murine embryos lacking the homeo box gene", Genes & Dev. 9:1654-1666 (1995).

Schaeren-Wiemers, N. et al., "A single protocol to detect transcripts of various types and expression levels in neural tissue and cultured cells: in situ hybridization using digoxigenin-labelled cRNA probes", Histochemistry, 100:431-440 (1993).

Galea, M. et al., "Corticospinal projection patterns following unilateral section of the cervical spinal cord in the newborn and juvenivle macaque monkey", Comp. Neurol., 381:282-306 (1997).

Rees, S. et al., "The structural and functional development of muscle spindles and their connections in fetal sheep", Brain Res., 642:185-198 (1994).

Adams, J. et al., "Heavy Metal Intensification of DAB-based HRP reaction product", Histochem. Cytochem., 29(6):775 (1981).

Capecchi, M. R.,. "Altering the genome by homologous recombination", Science, 244: 1288-1292 (1989).

DeFries, J. et al., "Response to 30 generations of selection for open-field activity in laboratory mice", Behavioural Genetics, 8(1):3-13 (1978).

Bregman, B. S. et al., "Anatomical plasticity and sparing of function after spinal cord damage in neonatal cats", Science, 217:553-555 (1982).

Bregman, B. S. et al., "Recovery from spinal cord injury mediated by antibodies to neurite growth inhibitors", Nature, 378:498-501 (1995).

Casale, E. J. et al., "Direct projection of the corticospinal tract to the superficial laminae of the spinal cord in the rat", Comp Neurology, 278:275-286 (1988).

Cohen, N. R. et al., "Errors in corticospinal axon guidance in mice lacking the neural cell adhesion molecule L1", Curr. Biol., 8:26-33 (1997).

Bastmeter. M. et al., "Dynamics of target recognition by interstitial axon branching along developing cortical axons", Neurosci., 16:1450-1459 (1996).

Holland. S. J. et al., "Bidirectional signaling through the EPH-family receptor Nuk and its transmembrane ligands", Nature, 383: 722-725 (1996).

Bruckner, K. et al., "Tyrosine phosphorylation of transmembrane ligands for Eph receptor", Science, 275:1640-1643 (1997).

Ohta, K. et al., "The inhibitory effect on neurite outgrowth of motoneurons exerted by the ligands ELF-1 and RAGS", Mech. Dev. 64:127-135 (1997).

Wang, H. U. et al., "Eph family transmembrane ligands can mediate repulsive guidance of trunk neural crest migration and motor axon outgrowth", Neuron, 18:383-396 (1997).

Richards, L. J. et al., "Directed growth of early cortical axons is influenced by a chemoattractant released from an intermediate target", Neurosci. 17(7):2445-2458 (1997).

Gilardi-Hebenstreit, P. et al., "An Eph-related receptor protein tyrosine kinase gene segmentally expressed in the developing mouse hindbrain", Oncogene, 7:2499-2506 (1992).

Laird, P. W. et al.,. Simplified mammalian DNA isolation procedure, Nucleic Acids Res., 19:4293 (1991).

Lackmann, M. et al. "Distinct subdomains of the Eph3 receptor mediate ligand binding and receptor dimerization", J. Biol. Chem., 273(32):20228-20237 (1998).

Lackmann, M. et al., "Ligand for Eph-related kinase (LERK) 7 is preferred high affinity ligand for the HEK receptor", J. Biol. Chem., 272(26):16521-16530 (1997).

Jensen, "Eph receptors and ephrins", Stem Cells, 18:63-64 (2000).

Holder & Klein, "Eph receptors and ephrins: effectors of morphogenesis",. Development, 126:2033-2044 (1999).

Bruckner & Klein, "Signaling by Eph receptor and their ephrin ligands", Current Opinion in Neurobiology, 8(3):375-382 (1998).

Pasquale, "The Eph family of receptors", Current Opinion in Cell Biology, 9(5):608-615 (1997).

Zisch & Pasquale, "The Eph family: a multitude of receptors that mediate cell recognition signals", Cell and Tissue Research, 290(2):217-226 (1997).

Flanagan & Vanderhaeghen, "The ephrins and Eph receptors in neural development", Annual Review of Neuroscience, 21:309-345 (1998).

The American Heritage® Dictionary of the English Language, Fourth Edition Copyright © 2000 by Houghton Mifflin Company.

Orioli & Klein, "The Eph receptor family: axonal guidance by contact repulsion", Trends Genet, 13(9):354 (1997).

Zhang et al., "Detection of ligands in regions anatomically connected to neurons expressing the Eph receptor Bsk: potential roles in neuron-target interaction", The Journal of Neuroscience, 16(22):7182-7192 (1996).

Castellani et al., "Dual action of ligand for Eph receptor tyrosine kinases on specific populations of axons during the development of cortical circuits", The Journal of Neuroscience, 18(12):4663-4672 (1998).

Jackowski, "Neural injury repair: hope for the future as barriers to effective CNS regeneration become earlier", Brithish Journal of Neurosurgery 9:303-317 (1995).

Kandel, "Principles in neural science", 4$^{th}$ Ed. Chapter 2 Nerve Cell and Behavior, pp. 19-35 (2002).

Dottori, et al., "EphA4 (Sek1) receptor tyrosine kinase is required for the development of the corticospinal tract", Proc. Natl. Acad. Sci. USA, vol. 95, pp. 13248-13253, Oct. 1998.

Zhou, "The Eph Family Receptors and Ligands", Pharmacol Ther., vol. 77, No. 3, pp. 151-181, 1998.

Goldshmit et al. "Axonal Regeneration and Lack of Astrocytic Gliosis in EphA4-Deficient Mice," The Journal of Neuroscience, 24(45):10064-10073, Nov. 10, 2004.

Howlett, K. et al., J. Biol. Chem., 272:16521 (1997).

Office Action issued Jul. 2, 2003, in U.S. Appl. No. 09/830,319, 5 sheets.

Office Action issued Feb. 18, 2004, in U.S. Appl. No. 09/830,319, 24 sheets.

Office Action issued Oct. 7, 2004, in U.S. Appl. No. 09/830,319, 9 sheets.

Office Action issued Jul. 25, 2006, in U.S. Appl. No. 100,716 , 15 sheets.

Final Office Action issued Apr. 16, 2007, in U.S. Appl. No. 11/100,716, 15 sheets.

International Search Report issued on Dec. 8, 2005, in application No. PCT/AU2005/001363.

Miranda et al., "Induction of Eph B3 after Spinal Cord Injury," *Experimental Neurology*, vol. 156, pp. 218-222 (1999).

Notice of Allowance issued on Oct. 15, 2007, by the Examiner in U.S. Appl. No. 11/100,716 (US 7,341,997).
Office Action issued on Apr. 16, 2007, by the Examiner in U.S. Appl. No. 11/100,716 (US 7,341,997).

Office Action issued on Jul. 25, 2006, by the Examiner in U.S. Appl. No. 11/100,716 (US 7,341,997).

* cited by examiner

A

B

C

Figure 3A:
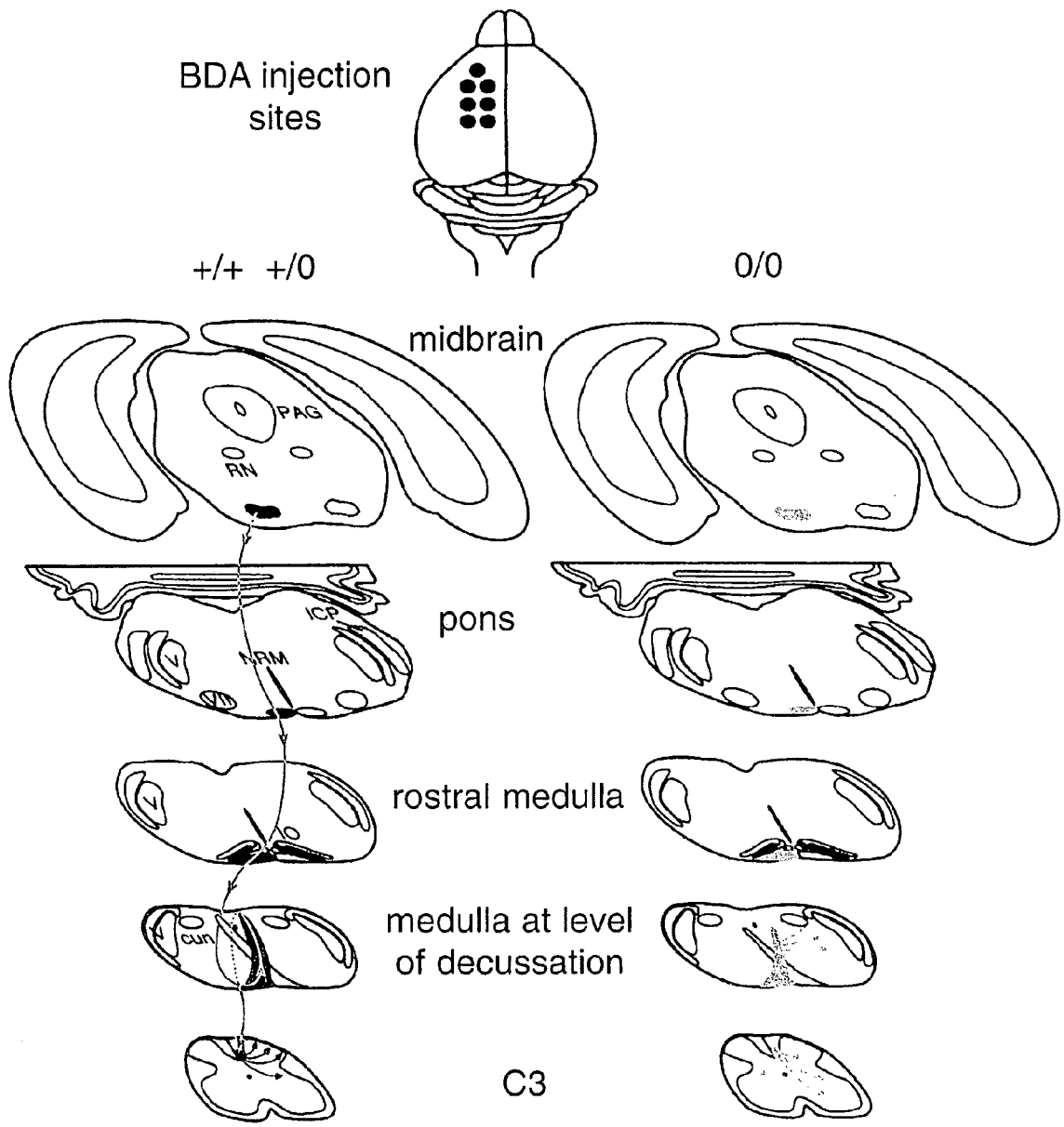

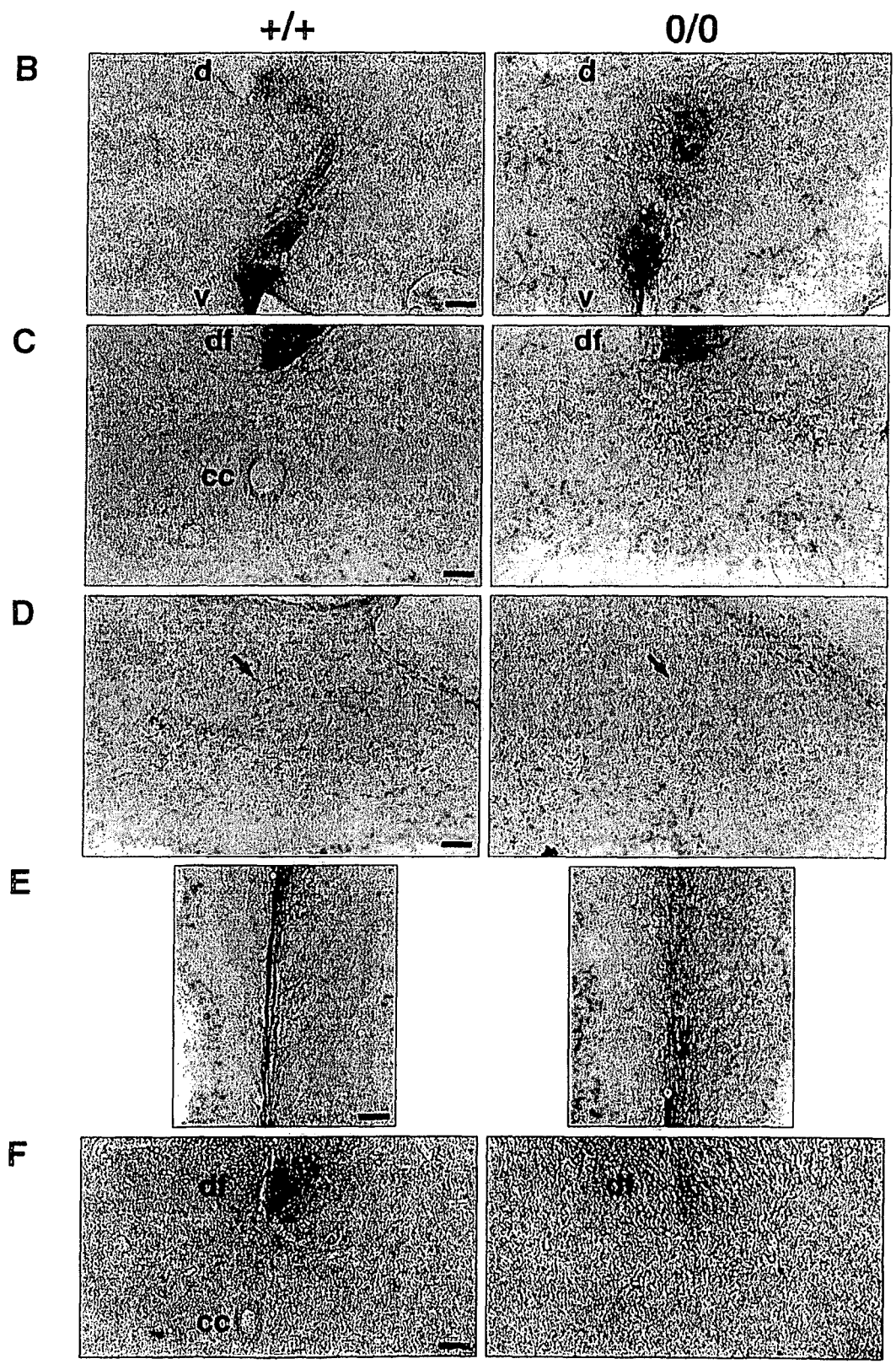
Figure 3 b,c,d,e,f

METHOD OF TREATMENT

The present invention relates generally to a method of treatment and in particular a method of treating disorders of the nervous system such as arising from or during disease or injury. The method of the present invention involves manipulating expression of Eph receptors or their functional equivalents to increase or decrease expression or function depending on the condition being treated.

Bibliographic details of the publications numerically referred to in this specification are collected at the end of the description. Sequence Identity Numbers (SEQ ID NOs.) for the nucleotide and amino acid sequences referred to in the specification are defined following the bibliography.

Recent studies show that axons are guided to their targets by a system of guidance molecules including Eph receptors and their ligands (1-3). The role of these molecules has been intensely studied in development of the visual system (4-6), where the reciprocal gradient expression of the Eph receptors in the retina and of their ligands in the optic tectum is the suggested basis for the formation of the retinotectal topographic map. Other observations pertinent to the role of these molecules in the developing nervous system include axonal fasciculation and establishing brain commissures (7-9).

The Eph family of receptors can be divided into two groups, EphA and EphB, based on the sequence similarities of their extracellular domain (10). Each EphA receptor is able to bind several Ephrin A ligands which are associated with the membrane via a GPI-linkage, these receptors show little or no binding to the transmembrane Ephrin B ligands (11, 12). The EphB group of receptors show the reverse pattern, binding predominantly to Ephrin B ligands. An exception to this 'rule' is the EphA4 (previously known as Sek1) receptor which was found to significantly bind to some of the transmembrane ligands in addition to all the GPI-linked ligands (11-13).

EphA4 expression during development shows a defined spatio-temporal pattern within the developing forebrain, hindbrain and mesoderm (14, 15). In the final stages of embryogenesis, expression of EphA4 is predominantly found within regions of the central nervous system, including the cerebral cortex, striatum, thalamus, hippocampus, and ventral spinal cord. In the hindbrain, EphA4 shows restricted expression to rhombomeres 3 and 5 (14) which suggested a role of this receptor in establishing boundaries during embryogenesis. This notion was supported by over expression of dominant negative, truncated EphA4 receptor in zebrafish embryos. The resultant mutant embryos were found to have disruption in the rhombomere boundaries and an expansion of the developing retina into the diencephalon (16, 17).

In work leading up to the present invention, the inventors generated laboratory animals deficient in the EphA4 receptor. The EphA4 mutant animals displayed a gross motor abnormality in the hindlimbs. Anatomical analyses and anterograde tracing of cortical neurons demonstrated a severe disruption of the corticospinal tract (CST) in these animals. The CST is the single longest axonal projection in the mammalian central nervous system (18). CST neurons arise from layer V in the neocortex and extend their axons through the forebrain, midbrain and hindbrain, and terminate at various levels of the spinal cord. In primates the CST axons predominantly synapse directly with the spinal motor neurons, whereas in the rodent most of the cortical axons synapse with interneurons which then connect to the spinal motor neurons. The EphA4 null mutant animals showed specific defects in the CST both at the level of the medulla and the spinal cord, which indicates that EphA4 is required for the correct formation of the CST.

Accordingly, one aspect of the present invention contemplates a method of facilitating regeneration, growth and/or development of a central nervous system and in particular the central nervous system in a human or non-human animal said method comprising increasing, elevating or otherwise enhancing the levels of a Eph receptor or its functional equivalent.

Another aspect of the present invention provides a method of regulating axon guidance in a human or non-human animal said method comprising increasing, elevating or otherwise enhancing the levels of an Eph receptor or its functional equivalent in said human or non-human animal.

Still another aspect of the present invention is directed to a method for facilitating the repair or replacement of axons in a human or non-human animal, said method comprising increasing, elevating or otherwise enhancing the levels of an Eph receptor or its functional equivalent in a region surrounding the cortex and/or inhibiting, reducing or otherwise down-regulating expression of the Eph receptor or its functional equivalent when expressed in tissues outside said region surrounding the cortex and which expression leads to blockage of axonal growth.

Yet another aspect of the present invention provides for a method of inducing, promoting or otherwise facilitating repair of nervous tissue in a human or non-human animal, said method comprising increasing, elevating or otherwise enhancing the levels of an Eph receptor or its functional equivalent in a region surrounding the cortex and/or inhibiting, reducing or otherwise down-regulating expression of the Eph receptor or its functional equivalent when expressed in tissues outside said region surrounding the cortex and which expression leads to blockage of axonal growth.

The repair of nervous tissue according to this aspect of the present invention may be required following or during disease or trauma. Particular diseases contemplated by the present invention include but are not limited to brain and spinal cord injury, diseases of the upper motor neuron and diseases of the central nervous system such as Alzheimer's disease, Parkinson's disease and multiple sclerosis.

The present invention may also be practiced by modulating levels of the ligands for Eph receptors or their functional equivalents, e.g. the ephrins or their functional equivalents. Particularly preferred ephrins include ephrin-B1, ephrin-B2 and ephrin-B3. The most preferred ephrin is ephrin-B3.

The method of the present invention may be accomplished in any number of ways including but not limited to administering soluble or near soluble forms of the Eph receptors or parts thereof (e.g. fragment comprising all or part of the extracellular domain) or their functional equivalents in monomeric, dimeric or other multimeric form. Administration may be in any convenient means such as directly into the spinal cord or brain. Since it is proposed, in accordance with the present invention, that the Eph receptors or their functional equivalents regulate axon guidance in the corticospinal tract (CST), the administration of a monomeric or multimeric form of the Eph receptors or parts thereof or ligands or their functional equivalents may assist in defining pathways for axon movement.

Where Eph receptors or their functional equivalents are expressed in inappropriate tissues, i.e. not in the region surrounding the CST, then soluble forms of epherins or other Eph antagonists may be administered, such as to the brain and/or spinal cord, to block the expression or function of the Eph receptors or their functional equivalents. An example of other Eph antagonists include receptor monomers or other derivatives or their functional equivalents. Labelled Eph monomers such as FLAG-tagged Eph monomers (40, 41) are particularly useful antagonists.

Reference herein to "Eph receptor" means the murine Eph receptor or a functional equivalent thereof such as a human or non-murine homologue. The present invention further extends to the manipulation of derivatives of the Eph receptor or its functional equivalent. A derivative includes a part, fragment or portion of the receptor such as a single or multiple amino acid substitution, deletion and/or addition to the amino acid sequence defining the Eph receptor or its functional equivalent. The present invention further extends to ligand binding portions of the Eph receptor such as an extracellular portion of the receptor. An example of a fragment of an Eph receptor having ligand binding capacity is U.S. patent application Ser. No. 09/104,340 entitled "Receptor ligand system and assay".

Derivatives also include single or multiple amino acid substitutions, deletions and/or additions to an Eph receptor or its functional equivalent or single or multiple nucleotide substitutions, deletions and/or additions to the genetic sequence encoding an Eph receptor or its functional equivalent. "Additions" to amino acid sequences or nucleotide sequences include fusions with other peptides, polypeptides or proteins or fusions to nucleotide sequences. Reference herein to an Eph receptor includes reference to all derivatives thereof including functional and non-functional derivatives as well as homologues and analogues thereof.

Analogues of an Eph receptor contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates chemical analogues of an Eph receptor capable of acting as antagonists or agonists of an Eph receptor or which can act as functional analogues of an Eph receptor. Chemical analogues may not necessarily be derived from an Eph receptor but may share certain conformational similarities. Alternatively, chemical analogues may be specifically designed to mimic certain physiochemical properties of an Eph receptor. Chemical analogues may be chemically synthesised or may be detected following, for example, natural product screening.

These types of modifications may be important to stabilise an Eph receptor if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

TABLE 1

| Non-conventional amino acid | Code |
| --- | --- |
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |

TABLE 1-continued

| Non-conventional amino acid | Code |
| --- | --- |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| Chexa L-N-methylhistidine | Nmhis |
| L-N-methylisoleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) | Nnbhe |

TABLE 1-continued

| Non-conventional amino acid | Code |
|---|---|
| carbamylmethyl)glycine | |

The present invention further contemplates modified animals with altered expression levels of an Eph receptor or its functional equivalent. Such modified animals include "knock-out" murine animals such as "knock-out" mice. Alternatively, the modified animals have increased expression levels of the Eph receptor or its functional equivalent or expression in particular tissue or targeting expression in a region surrounding the CST.

The preferred Eph receptor is EphA4 or its functional equivalent in murine species or non-murine species (e.g. humans).

The present invention further extends to agonists and antagonists of an Eph receptor such as EphA4 or its functional equivalent and pharmaceutical compositions comprising same. The present invention also extends to genetic molecules encoding the Eph receptor or its functional equivalent or encoding an agonist, antagonist or ligand thereof. Particularly useful antagonists comprise monomeric Eph receptor molecules or their functional equivalents, soluble forms of the Eph receptor ligands (e.g. ephrins) or molecules detected following screening of natural product or chemical libraries. Particularly useful ephrins include ephrin B3 and EphA4-binding ephrins.

The use of the expression of the Eph receptor to guide axonal movement has therapeutic implications including the use of Eph receptors to direct therapeutic molecules to particular targets.

The present invention is now further described with reference to the preferred Eph receptor, EphA4 and to a "knock-out" mouse for the EphA4 gene. This is done, however, with the understanding that the present invention extends to any Eph receptor or its functional equivalent which is involved in axonal guidance in humans or non-human animals. Reference to non-human animals include livestock animals (e.g. sheep, horses, pigs, donkeys, cows), laboratory test animals (e.g. mice, rats, guinea pigs, hamsters), companion animals (e.g. dogs, cats) and captured wild animals.

The EphA4 null (i.e. "knock-out") mutant mice are the first Eph receptor null mice to display a motor phenotype (7-9). This motor defect is more marked in the hindlimbs and the animals have an abnormal 'hopping' gait. Analysis of the CST in these animals reveal a reduced number of CST axons in the lower spinal cord segments and an abnormal pattern of termination at higher segments of the spinal cord and medulla. This progressive diminution of the CST, relative to normal animals, along the length of the cord is consistent with the more marked motor defect observed in the lower limbs of these animals. Additionally, it has been observed that some rats which have had their CST disrupted by transection also show a phenotype with a hopping gait similar to the EphA4 null mutants. Thus, a defective CST accounts for the motor defect.

The perturbation of the CST in null mutant animals establishes that EphA4 is required for CST development. During CST development, the first pioneering axons to advance down the spinal cord are those that will innervate the lumbar segments and these are then followed by a bulk of later arriving fasciculating CST fibres projecting to upper cord segments (18). As the primary growth cones of corticospinal axons continue to elongate down the midline of the spinal cord, the brainstem and spinal cord targets are contacted by collateral branches sprouted along the corticospinal axon shafts (32). The paucity of CST axons observed within the lumbar spinal cord regions in the EphA4 mutants are presumably due to misguidance of the primary cortical axons. It is possible that guidance of the collateral branches along the whole CST are also disrupted. Altogether, these data strongly indicate that EphA4 regulates axon guidance in the CST.

The immunohistochemistry and in situ hybridization data suggest that EphA4 is not expressed by cortical motor neurons or in the CST during its development. However, EphA4 was found highly expressed within the intermediate and ventral regions of the spinal cord which is the region where the CST axons do not normally terminate. This is consistent with the notion that EphA4 is expressed on structures surrounding the CST where it acts as a signal for CST axons bearing Ephrin ligands to be appropriately guided. Also consistent with this model, EphrinB3 mRNA was detected within the sensorimotor cortex at E18.5 which suggests that this transmembrane ligand is expressed on CST axons as they extend through the brain and spinal cord. EphA4 binds to EphrinB3 with high affinity and the transmembrane Ephrin ligands have been shown to induce signalling upon receptor binding (12, 13, 33, 34).

Both in vitro and in vivo studies have suggested that the Eph receptor family regulate axon guidance through mechanisms of contact repulsion rather than attraction (5, 6, 35, 36). For example, in EphB2 receptor-null mice the posterior tract of the AC innervates the floor of the brain aberrantly (7). EphB2 is normally expressed in areas ventral to the commissure and the commissural axons express a ligand for EphB2, Ephrin-B1. This suggests, therefore, that EphB2 repels AC axons from entering this ventral area via Ephrin-mediated signals (33, 34). The present invention is consistent with a similar mechanism relating to guidance of the CST.

Another molecule found to be involved in CST development is the neural cell adhesion molecule, L1. In mice deficient in L1 many of the CST axons failed to decussate at the medulla, passing ipsilaterally into the dorsal columns (31). Similar to EphA4 null mice, the number of CST axons within the dorsal funiculus of the spinal cord was reduced and these axons did not project beyond the cervical levels. It was proposed that the interaction of L1 on the axons with CD24 (expressed in the midline) may modify the CST axons response to midline inhibitory cues, thereby allowing the axons to cross the midline. Another molecule shown to act as a guidance cue for CST axons is Netrin-1 (37). It was shown that the pathfinding of CST axons from the cortex to the internal capsule of the forebrain may be mediated by the chemoattractive activity of Netrin-1. Although not intending to limit the present invention to any one theory or mode of action, it is proposed herein that CST axons are guided by the combined actions of a number of attractive and repulsive guidance cues.

The present invention provides intera alia an understanding of the role that EphA4 plays in mammalian neural development. The inventors show that EphA4 may not be required for initial corticospinal tract development and that it is also not required for adult pinal motoneuron morphological development and survival. However, the inventors do show that EphA4 plays an important role in the correct topographic positioning of some spinal cord motoneuron populations. EphA4 is expressed in specific areas of the brain during late embryonic development. These data provide an explanation for the axonal abnormalities observed in the EphA4 null mutant. The inventors show that EphA4 is widely expressed in the adult spinal cord after traumatic injury and this may contributed to the lack of axonal regeneration observed following spinal cord trauma. This knowledge of EphA4 expression after injury is important for the clinical treatment of spinal cord injury as well as other central nervous system diseases such as Alzheimer's disease, Parkinson's disease and multiple sclerosis.

The present invention is further described by the following non-limiting Figures and Examples.

Figure 4:
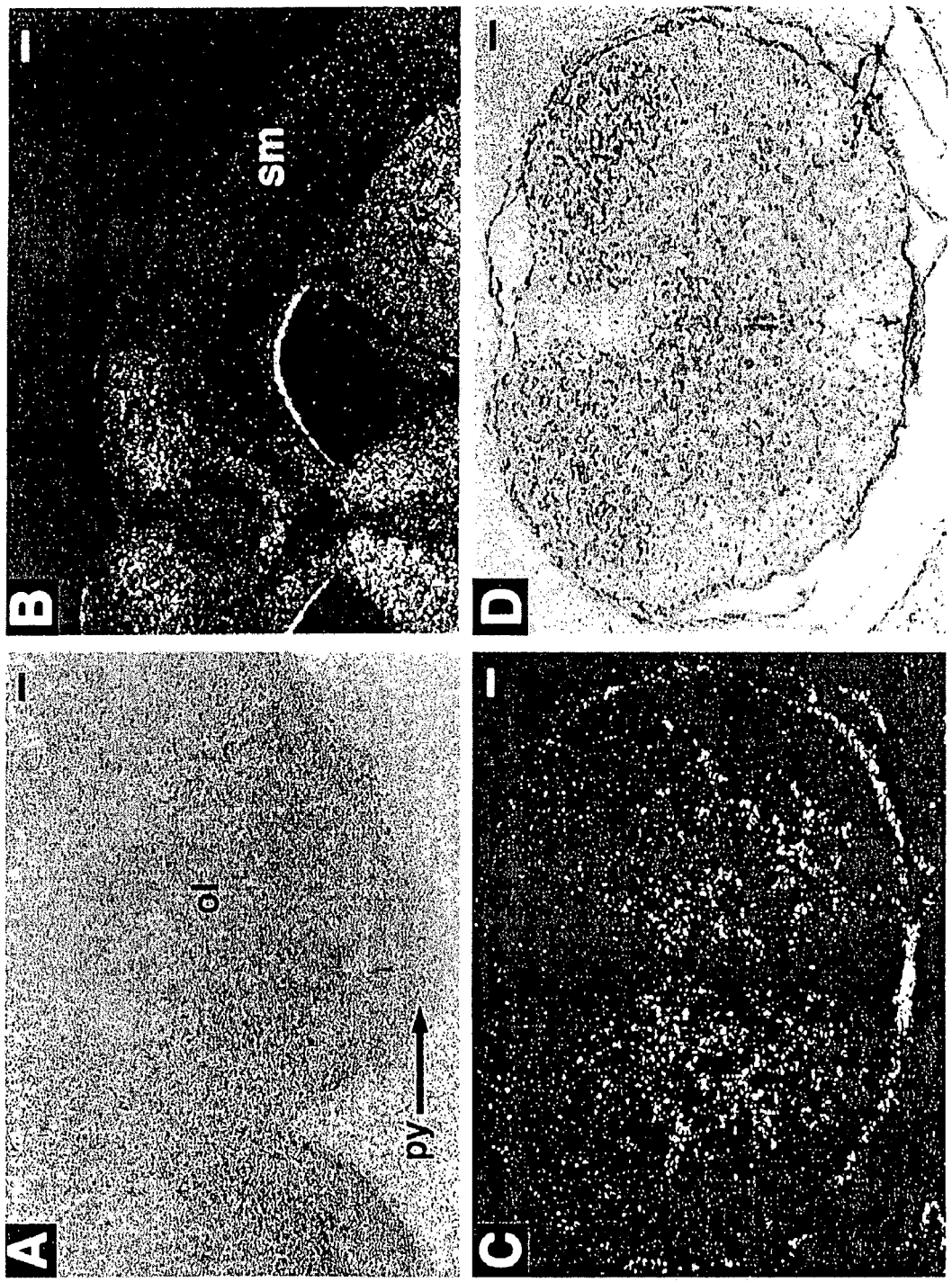

In the Figures:

FIG. 1 is a representation showing targeted disruption of EphA4 gene. (A) Partial map of the ephA4 genomic locus (+/+) with the targeting construct and the resulting targeted loci (o/o). The EphA4 targeting vector was designed to replace exon III (217 bp-880 bp of EphA4 cDNA) (38) with the 1.8 kb neomycin selection gene. For homologous recombination, 5' HindIII-SacI 3 kb sequence and 3' Eco47III-BamHI 5.5 kb sequence flanking exon III were subcloned into the pKJ1 vector. Homologous recombination would cause a frame shift in the EphA4 gene resulting in a null mutant protein (FIG. 4.2). The probe used for all Southern analysis was a 1 kb genomic fragment containing exon II (149 bp-216 bp) and EcoRI site. Ec, EcoRI; H, HindIII; S, SacI; E47, Eco47III; B, BamHI; Neo, neomycin gene; II, exon II; III, exon III. (B) Genotype analysis of EphA4 homozygous (o/o), heterozygous (+/o), and wild type (+/+) animals. Genomic DNA was isolated from 0.5 cm tail tissue (39), digested with EcoRI and subjected to Southern blot analysis using the 5' external probe shown in A. Alleles bearing the ephA4 mutation results in a 5 kb band, whereas an 11 kb band is observed in the wild type alleles. (C) Whole-mount immunocytochemistry of E8.5 embryos using anti-EphA4 antibody. EphA4 is expressed in rhombomeres 3 and 5 (arrows) in heterozygotes (+/o), but no EphA4 protein is detected in homozygous (o/o) mutants. The embryos were genotyped by PCR from yolk sac DNA.

Figure 2:
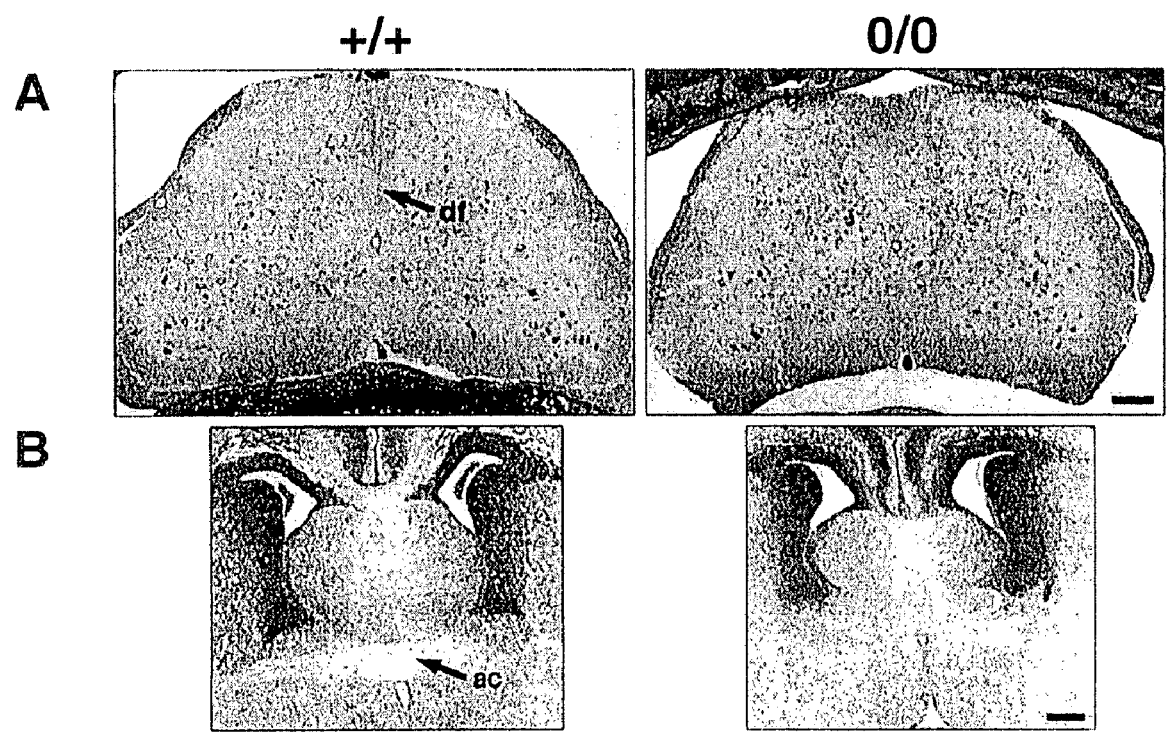

FIG. 2 is a photographic representation of histological sections of EphA4 homozygous (o/o) and wild type (+/+) animals. (A) Transverse sections stained with luxol fast blue of lumbar spinal cord from adult mice. Area of the dorsal funiculus (df) appears to be shallower in EphA4 homozygotes. Scale bar=160 µm. (B) Coronal sections stained with haematoxylin and eosin of E16 embryo brains. A loss of the anterior commissure (ac) is observed in homozygotes. Scale bar=140 µm.

FIG. 3 shows labelled CST in normal (+/+ and +/o) and EphA4 null mutant (o/o) mice. (A). Schematic representation of the corticospinal projection traced in mice. Multiple injections of the tracer was made in the motor cortex in the left cerebral hemisphere of adult mice. The labelled CST axons descend through the midbrain, pons and pyramid in the medulla. In wild type and heterozygous mice, the CST axons decussate at the medulla, crossing the midline travelling from left ventral to right dorsal, enter the dorsal funiculus of the spinal cord and terminate predominantly in the dorsal horn contralateral to the tracer injections. In EphA4 null mutant mice, labelled CST axons appeared to terminate in the medulla and intermediate and ventral region of the spinal grey matter. Some labelled fibres were observed to recross the midline. PAG, periaqueductal grey; ICP, inferior cerebellar peduncle; V, trigeminal nucleus; IO, inferior olive; RN, red nucleus; NRM, nucleus raphe magnus; VII, facial nucleus; cun, cuneate nucleus. (B) Transverse sections of medulla showing the decussation of labelled CST fibres travelling from left ventral (v) to right dorsal (d). In EphA4 o/o mice, many CST axons do not enter the dorsal column area. Scale bar=450 µm. (C and D) Transverse sections of cervical spinal cord showing area of dorsal funiculus (C) and dorsal horn (D). In wild type animals, labelled CST axons terminate in the right dorsal horn (arrow). In homozygotes, axons project predominantly into the intermediate and ventral regions of the grey matter, and no labelled axons were observed terminating in the dorsal horn. cc, central canal; df, dorsal funiculus. Scale bar=125 µm. (E) Longitudinal sections of cervical spinal cord. CST axons in the right dorsal funiculus are seen in the midline. In homozygous animals some CST fibres recross the midline and project to the grey matter ipsilateral to the tracer injections. Scale bar=300 µm. (F) Transverse sections of lumbar spinal cord. A reduced number of labelled CST axons was observed in the dorsal funiculus of the null mutant mice compared to normal. Scale bar=125 µm.

FIG. 4 is a photographic representation showing analysis of EphA4 expression in wild type neonatal mouse tissues by immunohistochemistry (A) and in situ hybridization (B and C). (A) Coronal section of the medulla stained with anti-EphA4 antibody. EphA4 was detected in the inferior olivary nucleus (ol), but not in the pyramidal tract (py). Scale bar=125 µm. (B) Dark-field photomicrograph showing a coronal section of brain hybridized with radiolabelled-antisense EphA4 probe. The level of EphA4 mRNA within the sensorimotor cortex (sm) region is not above background. Scale bar=420 µm. (C) Dark-field, and (D) bright-field, photomicrograph of cervical spinal cord transverse section hybridized with antisense EphA4 probe. EphA4 mRNA is found expressed within the intermediate and ventral regions of the spinal cord grey matter. df, dorsal funiculus. Scale bar=150 µm. No signal was observed in equivalent tissue sections stained with radiolabelled-sense probe.

Figure 5:
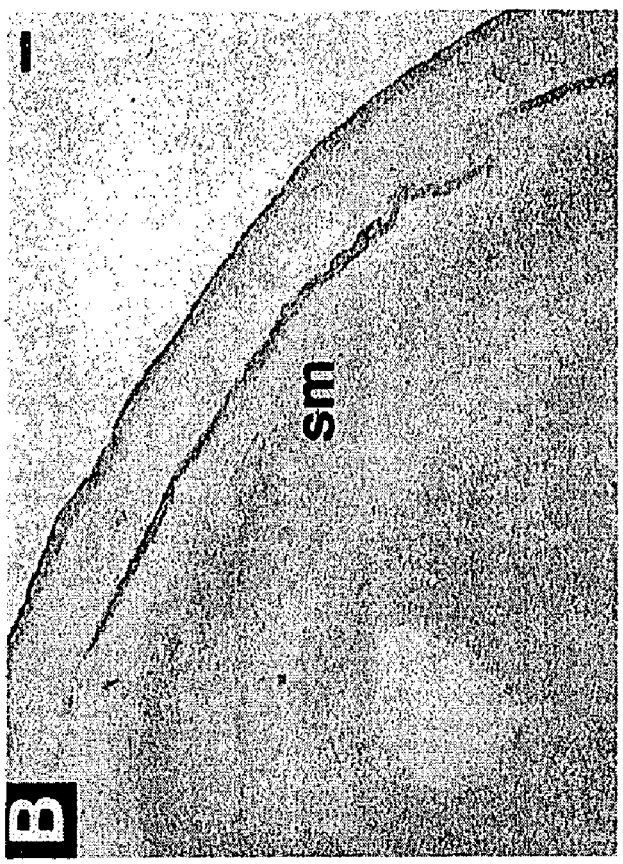
Figure 5:
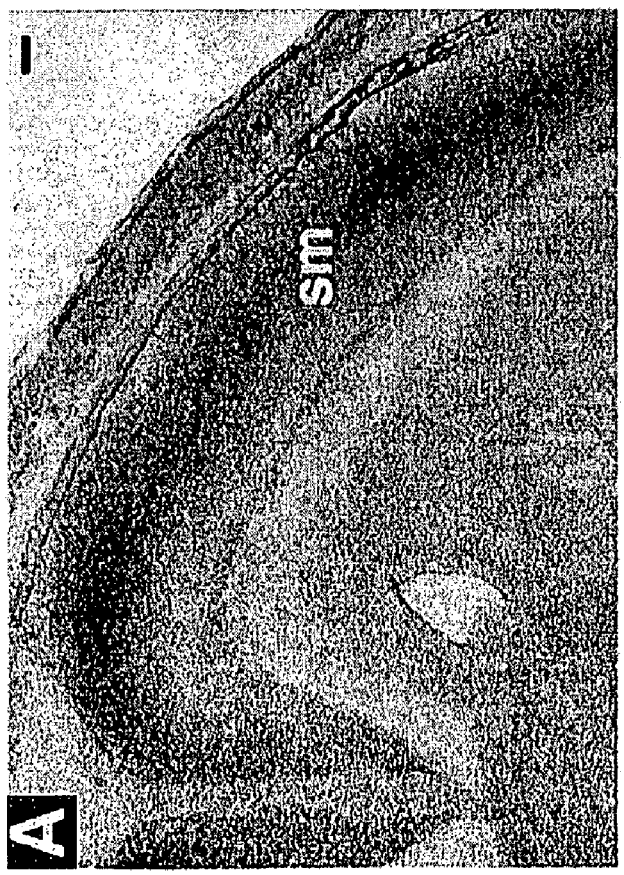

FIG. 5 is a photographic representation showing analysis of EphrinB3 expression in wild type E18.5 mouse tissue by in situ hybridization. Coronal sections of whole head were hybridized with DIG-labelled (A) antisense Ephrin B3 and (B) sense riboprobes. An intense signal of Ephrin B3 mRNA is detected within the sensorimotor (sm) cortex region. Scale bar=400 µm.

Figure 6:
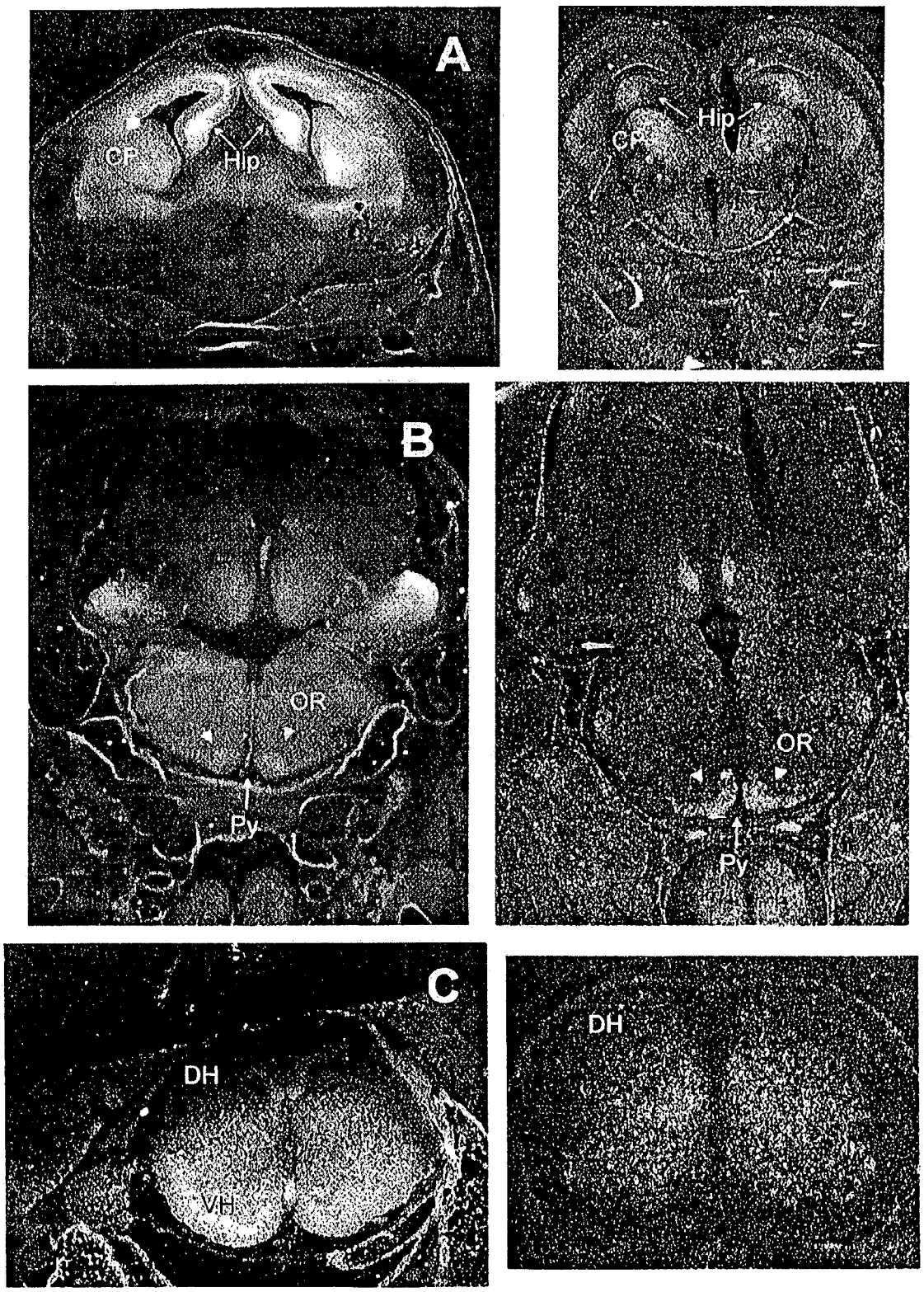

FIGS. 6A to C are photographic representations defining the localisation of EphA4 expression in the brain and spinal cord of a 17.5 day old mouse wild type embryo.

Figure 7:
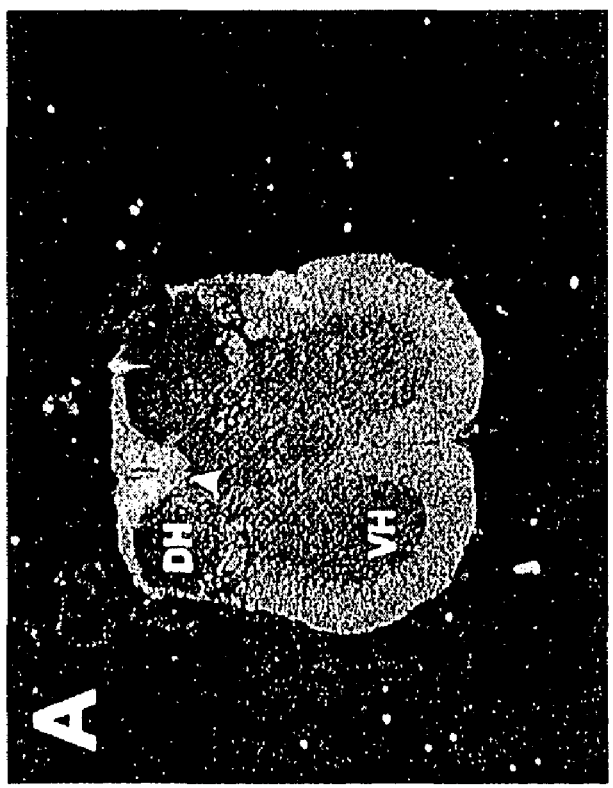
Figure 7:
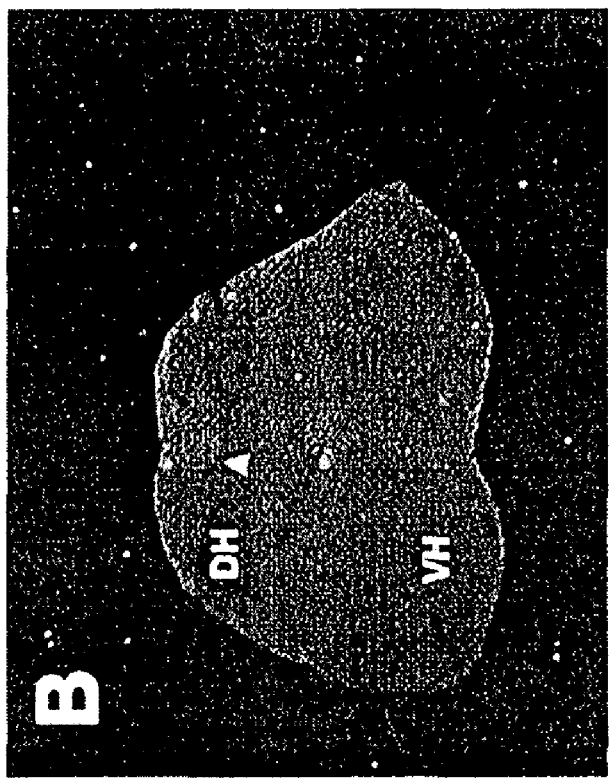

FIGS. 7A and B are photographic representations defining the localisation of EphA4 protein in cross sections of the adult spinal cord after a trauma injury (A) and in an uninjured control (B).

EXAMPLE 1

Materials and Methods

Targeted disruption of EphA4 gene. For homologous recombination, 5' HindIII-SacI 3 kb sequence and 3' Eco47III-BamHI 5.5 kb sequence flanking exon III were subcloned into the pKJ1 vector (FIG. 1). The vector contains the neomycin-resistance gene (neo) with the phosphoglycerate kinase (pgk) promoter and pgk polyadenylation signal. The W9.5 embryonic stem cell line was electroporated with the Sal I linearized targeting construct and selected with G418 for 10 days. A total of 480 surviving clones were expanded and homologous recombinants were identified by Southern analysis of genomic DNA from single clones digested with EcoR1. Two isolated clones with a single targeted mutation of EphA4 gene were each injected into (C57BL/6×C57BL/10) $F_2$ blastocysts. Chimeras were mated to C57BL/6 mice to produce heterozygotes. Southern analysis of tail DNA was used for genotyping the offspring.

Whole-mount and Tissue Immunocytochemistry and PCR Genotyping of Embryos. Whole-mount immunocytochemistry was performed with anti-EphA4 antibody (available from D. G. Wilkinson of NIMR, Mill Hill, UK) as previously described (19) and colour detection was carried out using BCIP/NBT (Promega) as substrate. For tissue sections, tissues were fixed for 24 hours in 4% v/v paraformaldehyde and then another 24 hours in fixative containing 30% w/v sucrose. Frozen tissue was serially sectioned 50 μm thick. Immunohistochemistry was performed using anti-EphA4 antibody and the same protocol as for whole mounts, except the ABC Elite detection system (Vector Laboratories, Burlingame Calif.) was used to detect colour staining.

Embryos were genotyped by PCR of yolk sac DNA (20) using primer pairs P1 CGTGCTACTTCCATTTGT-CACGTCCTG [SEQ ID NO:1] and P2 TGCCGTGATAG-CAAATTTGAG [SEQ ID NO:2] or P3 AGGAAGTGAG-CATTATGGATGA [SEQ ID NO:3] and P4 TGCTCCTCGTGCCCAGCGTT [SEQ ID NO:4]. A 600 bp band is generated from the mutant allele between the neomycin primer P1 and ephA4 endogenous primer P2; a 645 bp product is generated from the wild type allele between exon III primers, P3 and P4. The PCR reaction was in a total volume of 50 μl and consisted of 50-500 ng DNA, 30 pmoles of each primer, 2.0 mM MgCl, 100 μM dNTPs, 1 U Taq polymerase (Roche) with the appropriate reaction buffer supplied by the manufacturer. The cycling reaction was 15 cycles of 96° C. for 30 sec, 70° C. for 30 sec (−1° C. per cycle) and 72° C. for 1 min, followed by 20 cycles of 96° C. for 30 sec, 55° C. for 30 sec, and 72° C. for 1 min.

Histology. Histological examination was carried out on EphA4 homozygous, heterozygous and wild type littermates of embryonic age E16, 8 day and 24 day old mice. Embryos and adult tissues were fixed overnight in 10% v/v formalin, paraffin-embedded and serially sectioned 4 μm thick. Sections were stained with either haematoxylin and eosin or luxol fast blue.

In-situ Hybridization. For EphA4 mRNA expression, tissues were fixed overnight in 10% formalin, paraffin-embedded and serially sectioned 4 μm thick. In situ hybridization was performed as previously described (21) using $^{33}$P-radiolabeled complimentary EphA4 RNA probe. The antisense probe was synthesized with T7 polymerase from the HindIII-linearized plasmid Bluescript KS, containing a 1.5 kb EcoRI fragment of 3' untranslated and C-terminal coding sequences of EphA4 (provided by D. G. Wilkinson of NIMR, Mill Hill, UK).

For expression of EphrinB3 mRNA, DIG-labelled in situ hybridization was performed on frozen 20 μm tissue sections as previously described (22). To generate the Ephrin B3 probe, Ephrin B3 cDNA was amplified by PCR from adult mouse brain cDNA, using primers TTAGAATTCCCCGAG-GAGGAGCTGTAC [SEQ ID NO:5] and CTAGAATTCTG-CAGTCCCACCACCCCG [SEQ ID NO:6]. The PCR product, which spans 551 bp to 953 bp of Ephrin B3 cDNA (13), was cloned into EcoRI site of Bluescript SK and sequenced. The antisense probe was then synthesized with T3 polymerase from the HindIII-linearized plasmid.

Surgery, Anterograde Tracing and Tissue Processing. Corticospinal axons and their terminal projections were labelled in 5 week old mice using the anterograde tracer, Biotinylated Dextran Amine (BDA, 15%) (Molecular Probes, Eugene, ON). Two wild type, one heterozygous, and three homozygous EphA4 mutant mice were used for these studies. The animals were anaesthetised by injecting intraperitoneal (10 μl/gm body weight) a 1:1:6 ratio mixture of Hypnorm (Janssen, Oxford, UK), Hypemovel (Roche), and distilled $H_2O$. Anaesthetised animals had their head positioned in a stereotaxic frame and a craniotomy (3-4 mm in diameter) was made to expose the rostral half of the left cerebral hemisphere. Seven injections of 0.3 μl of tracer were made into the cerebral cortex at a depth of 0.5-1.0 mm below its surface using a glass pipette (tip diameter 50 μm) attached to a Hamilton syringe (23). The injections covered the whole sensorimotor region of the cerebral cortex. The number of injections, the injection sites and the amount of tracer used per injection were kept consistent between control and mutant animals. The brain and spinal cord were perfused 7 days following the injection with 0.9% w/v phosphate buffered saline and 4% v/v paraformaldehyde in phosphate buffer (PB). The tissue was postfixed for 24 hours in 30% w/v sucrose in buffered fixative.

The free-floating sections were processed according to the method as described (24) in order to visualise the axons and terminals labelled by BDA. Phosphate buffer (0.1M) was the vehicle for the immunoreagents and for rinsing after each of the following steps: (a) incubation in 0.3% v/v hydrogen peroxide in methanol for 20 mins to block any endogenous peroxidase activity (b) incubation in Avidin-peroxidase (Sigma) diluted 1:5,000 in 0.1M phosphate buffer and 0.75% v/v Triton X-100 for 2 hours (c) processing for horseradish peroxidase histochemistry using cobalt-enhanced diaminobenzidine (DAB) reaction (25) for 8-10 mins. This process stained the axons and terminals labelled with BDA black. Transverse spinal cord sections were counter-stained with haematoxylin.

EXAMPLE 2

Generation of EphA4 Homozygous Mice

EphA4 deficient mice were generated using targeted mutagenesis and embryonic-stem (ES) cell technology (26). The gene targeting strategy (FIG. 1A) replaces exon III with a neomycin selection gene thereby introducing a frame shift and stop codon in the ephA4 gene. To demonstrate that the EphA4 mutation results in a null mutation, whole-mount immunohistochemistry was performed on E8.5 embryos (FIG. 1C). In wild type and heterozygous embryos, EphA4 was expressed in rhombomeres 3 and 5 (arrows), as previously described (14). In contrast, no staining was observed in the EphA4 homozygous embryos. The antibody recognises the C-terminus of the intracellular domain (2783-3195 residues) of EphA4 (19) and thus, the lack of staining observed in the homozygous embryos implies that no EphA4 protein is produced in these mutant mice. EphA4 null mutant mice generated from two independent ES cell lines were viable and fertile. The number of EphA4 homozygous mice in litters born from crossing heterozygotes showed a normal Mendelian ratio (25%), indicating no lethality of the mutation during embryogenesis.

EXAMPLE 3

EphA4 Homozygous Mice Display an Abnormal Hopping Gait

The EphA4 null mice exhibited locomotor abnormalities with impairment of the coordinated movement of the limbs. Both mouse strains showed hesitation in initiating locomotion, and once they began to move there was lack of the normal synchronous movement of each forelimb with the contralateral hindlimb. Most striking was an abnormal, synchronous, "kangaroo-like" movement of the hindlimbs while reciprocal movement of the forelimbs was maintained. In contrast, the heterozygous mice showed no abnormality.

Tests of neurological function were performed to further characterize the defects in these animals. The hesitation to move and lack of co-ordination in the hindlimbs was reflected in open field activity tests (27) which showed the distance traveled by the EphA4 homozygotes was only 30% of the heterozygote value (EphA4 homozygotes crossed 18±24 grids per 5 minutes compared to heterozygous littermates which crossed 60±134 grids, n=15, p<0.0005). In addition, the EphA4 null mutant animals showed placing deficits of both hindlimbs, suggesting a defect in corticospinal projections (28, 29), whereas sensory tests were within normal limits.

EXAMPLE 4

Disruption of Spinal Cord Architecture and the Anterior Commissure in EphA4 Homozygous Mice Anatomical studies were performed to determine if there were major structural changes in the central nervous system of the EphA4 null mice. While there was no macroscopic abnormality, histological analysis of spinal cord sections showed that the dorsal funiculus was markedly shallower in the EphA4 null animals compared to heterozygous and wild type animals (FIG. 2A). The major motor pathway, the corticospinal tract (CST), descends through the dorsal funiculus in the rodent spinal cord. Anatomical studies revealed a further defect in the EphA4 null mutant mice, a loss of the anterior commissure (AC). This was observed in 12 of the 14 homozygous specimens examined (FIG. 2B), but appeared normal in all heterozygous and wild type mice. No other anatomical abnormalities were observed in the brains of EphA4 mutants, including within the motor cortex, midbrain, and medullary pyramids.

EXAMPLE 5

Corticospinal Projection is Aberrant in EphA4 Homozygous Mice

Functional tests and the abnormality in the dorsal funiculus suggested that the CST may be disrupted or absent in EphA4 deficient mice. This possibility was explored using dye tracing studies. Corticospinal axons were anterogradely labelled from their origin, layer V neurons in the motor cortex, to their terminal projections. Normally CST axons descend through the internal capsule, basis pedunculi in the midbrain, pons and medullary pyramids (FIG. 3). In the medulla the CST fibres cross the midline (decussate), then descend in the dorsal funiculus of the spinal cord and terminate predominantly in the dorsal horn contralateral to the cells of origin.

Anterograde labelling of corticospinal neurons in EphA4 null mice showed normal projection within the fore- and mid-brain. However, the CST pathway within the medulla and spinal cord was clearly abnormal. It was observed in the medulla that, while many of the CST axons crossed the midline, a considerable number of axons appeared to terminate inappropriately at this level, so that a reduced number of axons descended in the dorsal column of the spinal cord (FIG. 3B). In addition, those axons which descended in the dorsal funiculus showed an aberrant pattern of termination within the grey matter of the spinal cord (FIGS. 3C and 3D), with terminal branches observed predominantly in the intermediate zone and ventral horn and very few terminals in the dorsal horn. A number of axons also recrossed the midline and terminated in the grey matter ipsilateral to the cortical tracer injection (FIG. 3E). In the lumbar cord, there was a significant reduction in the number of CST axons (FIG. 3F), making it difficult to demonstrate whether their pattern of termination was also aberrant at this level.

A small proportion of CST axons do not decussate in the medulla, but continue to descend ipsilaterally into the spinal cord in the ventral funiculus (30). The ipsilateral CST found within the ventral funiculus does not appear to be notably different in homozygous, heterozygous and wild type animals.

EXAMPLE 6

Expression of EphA4 and Ligand During CST Development

To determine whether EphA4 protein was expressed in the CST, immunohistochemical studies were undertaken on neonatal mouse brain tissues, which is the period when the CST projects through the medulla and enters the spinal cord (31, 32). EphA4 protein was not detected within the medullary pyramid or any other part of the CST at this age, however, it is expressed in the olivary nucleus which is dorsal to the pyramidal tract (FIG. 4A). In addition, in situ hybridization studies were undertaken to determine whether EphA4 mRNA was detected within the motor cortex, which is where the cell bodies of the CST are localized. Consistent with the immunohistochemistry data, in situ hybridization analysis shows levels of EphA4 mRNA within the sensorimotor cortex which are not above background (FIG. 4B). However, a gradient expression of EphA4 mRNA was found within the spinal cord with high levels of expression detected in the intermediate and ventral regions of the spinal cord grey matter and low levels of expression in the dorsal horns (FIG. 4C). This data indicate that EphA4 is not expressed in the CST axons but is found expressed in surrounding structures.

To determine whether a ligand for EphA4 may be expressed in the CST, the inventors analysed the expression of Ephrin B3 within E18.5 mouse brain tissue (FIG. 5). Of the transmembrane ligands, Ephrin B3 binds to EphA4 with the highest affinity (12, 13). In situ hybridization with the DIG-labelled Ephrin B3 antisense probe detected strong expression within the sensorimotor cortex region (FIG. 5A) thereby suggesting that Ephrin B3 is expressed in the motor neurons of the CST during its development.

EXAMPLE 7

EphA4 Does not Play a Significant Role in the Early Embryonic Development of the CST In this experiment, corticofugalaxons are labelled with DiI in coronal sections of W/W and O/O E14 brains. Corticofugal axons in the O/O exhibited no obvious growth abnormalities at this stage and the number of processes reaching the inernal capsule (IC) is not reduced, indicating that disruption of EphA4 does not greatly affect initial process guidance or neuronal viability.

EXAMPLE 8

EphA4 Does Not Significantly Affect Lumbar Spinal Cord Motoneuron Survival

Lumbar spinal motoneurons were retrogradely labelled in the W/W and O/O using the fluorescent tracers Tetramethylrhodamine and Fast Blue. Mononeurons of the O/O exhibited no obvious morphological differences when compared to the W/W. Furthermore, when the numbers of retrogradely labelled motoneurons that innervate the sciatic nerve are stereologically counted. Results indicated that there is no significant difference between the numbers of motoneurons in the W/W and O/O indicating that EphA4 may not be required for survival of some populations of lumbar spinal motoneurons.

EXAMPLE 9

EphA4 May be Required for the Correct Topographic Positioning of Some Lumbar Spinal Cord Motoneuron Populations Labelling discrete lumbar spinal motoneuron populations with various fluorescent tracers revealed that in the O/O, the population of motoneurons that innervate the tibialis anterior muscle appear to have migrated further caudally than those observed in the W/W. In contrast, the motoneuron populations innervating the gastrocnemius muscle and sciatic nerve in the O/O appear to be topographically similar to the homologous populations labelled in the W/W.

EXAMPLE 10

EphA4 is Expressed in Specific Areas During Brain Development

Shown in FIGS. 6A-C are photographic representations defining the localisation of EphA4 expression in the brain and spinal cord of a 17.5 day old mouse wild type embryo. Left panel: localisation of EphA4 receptor protein by immunohistochemistry using an EphA4 specific antibody and fluorescence staining. Right panel: localisation of EphA4 messenger RNA (mRNA) by in situ hybridisation using a radiolabeled EphA4 specific antisense probe (positive labelling appears as clusters of white dots).

A. Cross section through the brain in the region of the hippocampus (Hip). EphA4 expression is found in the hippocampus, sensorimotor cortex (Sm) and the caudate putamen (Cp).

B. Cross section through the medullary region of the brain. EphA4 protein expression was not detected within the medullary pyramid (Py) or any other part of the CST during any stage of development, but both EphA4 mRNA and protein was found to be strongly expression in the olivary region (OR), which is directly dorsal to the pyramidal tract.

C. Cross section through the cervical spinal cord. EphA4 protein and mRNA is found in the intermediate and ventral regions of the spinal cord grey matter but not in the dorsal horns.

These data indicate that EphA4 is not expression on the CST axons but is expression in the surrounding environment through which they grow.

EXAMPLE 11

EphA4 Protein is Expressed Following Spinal Cord Trauma

Shown in FIGS. 7A and B are photographic representations defining the localisation of EphA4 protein in cross sections of the adult spinal cord after a trauma injury (A) and in an uninjured control (B). Strong EphA4 expression is found in the injured spinal cord predominantly in the white matter (WM). The white matter surrounds the dorsal and ventral horns (DH and VH) of the spinal cord and is the area where axon tracts ascend and descend. Note that expression is found in dorsal funiculus (arrowhead) which is where the CST descends the spinal cord. No EphA4 expression is found in the uninjured spinal cord.

These data indicate that large areas of EphA4 expression after injury may inhibit regeneration of new axons in the adult spinal cord.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Brambilla, R. & Klein, R. (1995) *Mol. Cell. Neurosci* 6, 487-495.
2. Tessier-Lavigne, M. (1995) *Cell* 82, 345-348.
3. Friedman, G. C. & O'Leary, D. D. M. (1996) *Curr. Opin. Neurobiol* 6, 127-133.
4. Cheng, H. J., Nakamoto, M., Bergemann, A. D. & Flanagan, J. G. (1995) *Cell* 82, 371-381.
5. Drescher, U., Kremoser, C., Handwerker, C., Loschinger, J., Noda, M. & Bonhoeffer, F. (1995) *Cell* 82, 359-370.
6. Nakamoto, M., Cheng, H. J., Friedman, G. C., McLaughlin, T., Hansen, M. J., Yoon, C. H., O'Leary, D. D. M. & Flanagan, J. G. (1996) *Cell* 86, 755-766.
7. Henkemeyer, M., Orioli, D., Henderson, J. T., Saxton, T. M., Roder, J., Pawson, T. & Klein, R. (1996) *Cell* 86, 3546.
8. Orioli, D., Henkemeyer, M., Lemke, G., Klein, R. & Pawson, T. (1996) *EMBO J* 15, 6035-6049.
9. Park, s., Frisen, J. & Barbacid, M. (1997) *EMBO J* 16, 3106-3114.
10. Orioli, D. & Klein, R. (1997) *TIG* 13, 354-359.
11. Gale, N. W., Holland, S. J., Valenzuela, D. M., Flenniken, A., Pan, L., Ryan, T. E., Henkemeyer, M., Strebhard, K., Hirai, H., Wilkinson, D. G., Pawson, T., Davis, S. & Yancopoulos, G. D. (1996) *Neuron* 17, 9-19.
12. Gale, N. W., Flenniken, A., Compton, D. C., Jenkins, N., Copeland, N. G., Gilbert, D. J., Davis, S., Wilkinson, D. G. & Yancopoulos, G. D. (1996) *Oncogene* 13, 1343-1352.
13. Bergemann, A. D., Zhang, L., Chiang, M., Brambilla, R., Klein, R. & Flanagan, J. G. (1998) *Oncogene* 16, 471-480.
14. Nieto, M. A., Gilardi-Hebenstreit, P., Charnay, P. & Wilkinson, D. G. (1992) *Development* 116, 1137-1150.
15. Mori, T., Wanaka, A., Taguchi, A., Matsumoto, K. & Tohyama, M. (1995) *Brain Res. Mol. Brain Res.* 29, 325-335.
16. Xu, Q., Alidus, G., Holder, N. & Wilkinson, D. G. (1995) *Development* 121, 4005-4016.
17. Xu, Q., Alldus, G., Macdonald, R., Wilkinson, D. G. & Holder, N. (1996) *Nature* 381, 319-322.
18. Stanfield, B. B. (1992) *Prog. Neurobiol.* 38, 169-202.
19. Irving, C., Nieto, M. A., DasGupta, R., Charnay, P. & Wilkinson, D. G. (1996) *Dev. Biol.* 173, 26-38.
20. Robb, L., Lyons, I., Ruili, L., Hartley, L., Kontgen, F., Harvey, R. P., Metcalf, D. & Begley, C. G. (1995) *Proc Natl Acad Sci USA* 92, 7075-7079.
21. Lyons, I., Parsons, L. M., Hartley, L., Li, R., Andrews, J. E., Robb, L. & Harvey, R. P. (1995) *Genes & Dev.* 9, 1654-1666.
22. Schaeren-Wiemers, N. & Gerfin-Moser, A. (1993) *Histochemistry* 100, 431-440.

23. Galea, M. & Darian-Smith, I. (1997) *J. Comp. Neurol* 381, 282-306.
24. Rees, S., Rawson, J., Nitsos, I. & Brumley, C. (1994) *Brain Res.* 642, 185-198.
25. Adams, J. (1981) *J. Histochem. Cytochem.* 29, 775.
26. Capecchi, M. R. (1989) *Science* 244, 1288-1292.
27. DeFries, J., Gervais, M. & Thomas, E. (1978) *Behavioural Genetics* 8, 3-13.
28. Bregman, B. S. & Goldberger, M. E. (1982) *Science* 217, 553-555.
29. Bregman, B. S., Kunkel-Bagden, E., Schnell, L., Dai, H. N., Gao, D. & Schwab, M. E. (1995) *Nature* 378, 498-501.
30. Casale, E. J., Light, A. R. & Rustioni, A. (1988) *J Comp Neurology* 278, 275-286.
31. Cohen, N. R., Taylor, J. S. H., Scott, L. B., Guillery, P., Soriano, P. & Furley, A. J. W. (1997) *Curr. Biol.* 8, 26-33.
32. Bastmeyer, M. & O'Leary, D. D. M. (1996) *J Neurosci* 16, 1450-1459.
33. Holland, S. J., Gale, N. W., Mbamalu, G., Yancopoulos, G. D., Henkemeyer, M. & Pawson, T. (1996) *Nature* 383, 722-725.
34. Brückner, K., Pasquale, E. B. & Klein, R. (1997) *Science* 275, 1640-1643.
35. Ohta, K., Iwamasa, H., Drescher, U., Terasaki, H. & Tanaka, H. (1997) *Mech. Dev.* 64, 127-135.
36. Wang, H. u. & Anderson, D. J. (1997) *Neuron* 18, 383-396.
37. Richards, L. J., Koester, S. E., Tuttle, R. & O'Leary, D. D. M. (1997) *J. Neurosci* 17, 2445-2458.
38. Gilardi-Hebenstreit, P., Nieto, M. A., Frain, M., Mattei, M. G., Chestier, A., Wilkinson, D. G. & Charnay, P. (1993) *Oncogene* 8, 1103.
39. Laird, P. W., Zidervelt, A., Linders, K., Rudnicki, M. A., Jaenisch, R. & Berns, A. (1991) *Nucleic Acids Res.* 19, 4293.
40. Lackmann, M. et al. (1998) *J. Biol. Chem.* 273, 20228.
41. Howlett, K. et al. (1997) *J. Biol. Chem.* 272, 16521.

The invention claimed is:

1. A method of facilitating repair of nervous tissue in a mammal following spinal cord trauma comprising administering a soluble EphA4-binding ephrin to a mammal in need thereof.

2. The method according to claim 1, wherein the mammal is a human.

3. The method according to claim 1, wherein the mammal is an adult.

4. The method according to claim 1, wherein the soluble EphA4-binding ephrin is administered into the mammal's spinal cord.

* * * * *

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: PCR primer

<400> SEQUENCE: 1
cgtgctactt ccatttgtca cgtcctg                27

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
tgccgtgata gcaaatttga g                21

<210> SEQ ID NO 3
<211> LENGTH: 22
<212> TYPE: DNA
<213> ORGANISM: Artificial Sequence
<220> FEATURE:
<223> OTHER INFORMATION: PCR primer

<400> SEQUENCE: 3
aggaagtgag cattatggat ga                22

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
tgctcctcgt gcccagcgtt                20

<210> SEQ ID NO 5
<211> LENGTH: 27
<212> TYPE: DNA

```
<213> ORGANISM: Artificial Sequence
<220> FEATURE:
<223> OTHER INFORMATION: PCR primer

<400> SEQUENCE: 5
ttagaattcc ccgaggagga gctgtac                                               27

<210> SEQ ID NO 6
<211> LENGTH: 27
<212> TYPE: DNA
<213> ORGANISM: Artificial Sequence
<220> FEATURE:
<223> OTHER INFORMATION: PCR primer

<400> SEQUENCE: 6
ctagaattct gcagtcccac caccccg                                               27
```